(12) United States Patent
Lipkens et al.

(10) Patent No.: US 11,420,136 B2
(45) Date of Patent: Aug. 23, 2022

(54) AFFINITY CELL EXTRACTION BY ACOUSTICS

(71) Applicant: FloDesign Sonics, Inc., West Springfield, MA (US)

(72) Inventors: Bart Lipkens, Bloomfield, CT (US); Rudolf Gilmanshin, Framingham, MA (US); Natalia Rodionova, Framingham, MA (US); Benjamin Ross-Johnsrud, Northampton, MA (US)

(73) Assignee: FloDesign Sonics, Inc., West Springfield, MA (US)

( * ) Notice: Subject to any disclaimer, the term of this patent is extended or adjusted under 35 U.S.C. 154(b) by 673 days.

(21) Appl. No.: 15/788,784

(22) Filed: Oct. 19, 2017

(65) Prior Publication Data

US 2018/0104620 A1  Apr. 19, 2018

Related U.S. Application Data

(60) Provisional application No. 62/410,312, filed on Oct. 19, 2016.

(51) Int. Cl.
| | |
|---|---|
| B01D 15/38 | (2006.01) |
| C07K 17/10 | (2006.01) |
| B01D 21/28 | (2006.01) |
| C07K 1/14 | (2006.01) |
| C12N 1/02 | (2006.01) |
| C12N 13/00 | (2006.01) |
| G01N 33/543 | (2006.01) |
| C12M 1/00 | (2006.01) |

(52) U.S. Cl.
CPC ....... *B01D 15/3828* (2013.01); *B01D 21/283* (2013.01); *C07K 1/14* (2013.01); *C07K 17/10* (2013.01); *C12M 47/02* (2013.01); *C12M 47/04* (2013.01); *C12M 47/10* (2013.01); *C12N 1/02* (2013.01); *C12N 13/00* (2013.01); *G01N 33/54313* (2013.01)

(58) Field of Classification Search
None
See application file for complete search history.

(56) References Cited

U.S. PATENT DOCUMENTS

| | | | |
|---|---|---|---|
| 2,473,971 A | 6/1949 | Ross | |
| 2,667,944 A | 2/1954 | Crites | |
| 3,372,370 A | 3/1968 | Cyr | |
| 3,555,311 A | 1/1971 | Weber | |
| 4,055,491 A | 10/1977 | Porath-Furedi | |
| 4,065,875 A | 1/1978 | Srna | |
| 4,118,649 A | 10/1978 | Schwartzman et al. | |
| 4,158,629 A | 6/1979 | Sawyer | |
| 4,165,273 A | 8/1979 | Azarov et al. | |
| 4,173,725 A | 11/1979 | Asai et al. | |
| 4,204,096 A | 5/1980 | Barcus et al. | |
| 4,254,661 A | 3/1981 | Kossoff et al. | |
| 4,320,659 A | 3/1982 | Lynnworth et al. | |
| 4,344,448 A | 8/1982 | Potts | |
| 4,398,325 A | 8/1983 | Piaget et al. | |
| 4,484,907 A | 11/1984 | Sheeran, Jr. | |
| 4,552,669 A | 11/1985 | Sekellick | |
| 4,666,595 A | 5/1987 | Graham | |
| 4,673,512 A | 6/1987 | Schram | |
| 4,699,588 A | 10/1987 | Zinn et al. | |
| 4,743,361 A | 5/1988 | Schram | |
| 4,759,775 A | 7/1988 | Peterson et al. | |
| 4,800,316 A | 1/1989 | Wang | |
| 4,821,838 A | 4/1989 | Chen | |
| 4,836,684 A | 6/1989 | Javorik et al. | |
| 4,860,993 A | 8/1989 | Goode | |
| 4,878,210 A | 10/1989 | Mitome | |
| 4,983,189 A | 1/1991 | Peterson et al. | |
| 5,059,811 A | 10/1991 | King et al. | |
| 5,062,965 A | 11/1991 | Bernou et al. | |
| 5,085,783 A | 2/1992 | Feke et al. | |
| 5,164,094 A | 11/1992 | Stuckart | |
| 5,225,089 A | 7/1993 | Benes et al. | |
| 5,371,429 A | 12/1994 | Manna | |
| 5,395,592 A | 3/1995 | Bolleman et al. | |
| 5,431,817 A | 7/1995 | Braatz et al. | |
| 5,443,985 A | 8/1995 | Lu et al. | |
| 5,452,267 A | 9/1995 | Spevak | |

(Continued)

FOREIGN PATENT DOCUMENTS

| | | |
|---|---|---|
| AU | 2002236405 | 9/2002 |
| CN | 105 087 788 A | 11/2015 |

(Continued)

OTHER PUBLICATIONS

Neurauter, Axl A., et al. "Cell isolation and expansion using Dynabeads®." Cell separation. Springer, Berlin, Heidelberg, 2007. 41-73. (Year: 2007).*

Loos, Cornelia, et al. "Functionalized polystyrene nanoparticles as a platform for studying bio-nano interactions." Beilstein journal of nanotechnology 5.1 (2014): 2403-2412. (Year: 2014).*

Alvarez et al.; ShockWaves, vol. 17, No. 6, pp. 441-447, 2008.

Augustsson et al., Acoustophoretic microfluidic chip for sequential elution of surface bound molecules from beads or cells, Biomicrofluidics, Sep. 2012, 6(3):34115.

(Continued)

*Primary Examiner* — Robert J Yamasaki

(74) *Attorney, Agent, or Firm* — FloDesign Sonics, Inc.

(57) ABSTRACT

Beads with functionalized material applied to them are exposed to an acoustic field to trap or pass the beads. The beads may include or be free of ferro magnetic material. The beads may be biocompatible or biodegradable for a host. The size of the beads may vary over a range, and/or be heterogenous or homogenous. The composition of the beads may include high, neutral or low acoustic contrast material. The chemistry of the functionalized material may be compatible with existing processes.

14 Claims, 13 Drawing Sheets

(56) References Cited

U.S. PATENT DOCUMENTS

| | | |
|---|---|---|
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,562,823 A | 10/1996 | Reeves |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,674,630 B2 | 3/2010 | Siversson |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,605,074 B2 | 3/2017 | Shah |
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 | 6/2017 | Lipkens et al. |
| 9,670,938 B2 | 6/2017 | Beliavsky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 9,810,665 B2 | 11/2017 | Fernald et al. |
| 9,833,763 B2 | 12/2017 | Fernald et al. |
| 9,869,659 B2 | 1/2018 | Buckland et al. |
| 9,872,900 B2 | 1/2018 | Ciaramella et al. |
| 9,873,126 B2 | 1/2018 | Mao et al. |
| 9,873,894 B2 | 1/2018 | Conway et al. |
| 9,878,056 B2 | 1/2018 | Bancel et al. |
| 9,878,536 B2 | 1/2018 | Foresti et al. |
| 9,879,087 B2 | 1/2018 | DeSander et al. |
| 9,990,297 B2 | 1/2018 | Conway et al. |
| 9,907,846 B2 | 3/2018 | Morein et al. |
| 9,908,288 B2 | 3/2018 | Harkness |
| 9,909,117 B2 | 3/2018 | Kaduchak |
| 9,909,313 B1 | 3/2018 | Grubbs |
| 9,913,656 B2 | 3/2018 | Stulen |

(56) References Cited

U.S. PATENT DOCUMENTS

| | | |
|---|---|---|
| 9,913,866 B2 | 3/2018 | O'Shea et al. |
| 9,925,277 B2 | 3/2018 | Almarsson et al. |
| 9,926,382 B2 | 3/2018 | Fischer et al. |
| 9,937,207 B2 | 4/2018 | Gregory et al. |
| 9,938,390 B2 | 4/2018 | Storti et al. |
| 9,943,599 B2 | 4/2018 | Gehl et al. |
| 9,944,702 B2 | 4/2018 | Galetto |
| 9,944,709 B2 | 4/2018 | Galetto |
| 9,994,743 B2 | 4/2018 | El-Zahab |
| 9,974,898 B2 | 5/2018 | Spain et al. |
| 10,550,382 B2 | 2/2020 | Lipkens et al. |
| 10,640,760 B2 | 5/2020 | Lipkens et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0057886 A1 | 3/2004 | Jona Zumeris et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0138108 A1 | 6/2007 | Hadfield et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2009/0311800 A1* | 12/2009 | Bond ............... G01N 33/49 436/501 |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0033922 A1* | 2/2011 | Landers .......... B01L 3/502761 435/325 |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0207225 A1 | 8/2011 | Mehta et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0154795 A1 | 6/2014 | Lipkens et al. |
| 2014/0319077 A1 | 10/2014 | Lipkens et al. |
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0252317 A1 | 9/2015 | Lipkens et al. |
| 2015/0253226 A1 | 9/2015 | Augustsson et al. |
| 2015/0274550 A1 | 10/2015 | Lipkens et al. |
| 2015/0321129 A1 | 11/2015 | Lipkens et al. |
| 2016/0016180 A1* | 1/2016 | Lopez ............. B01L 3/502761 506/12 |
| 2016/0060615 A1 | 3/2016 | Walther et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |

(56) References Cited

U.S. PATENT DOCUMENTS

| | | |
|---|---|---|
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III et al. |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot et al. |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao et al. |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0080423 A1 | 3/2017 | Dauson et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarty et al. |
| 2017/0128523 A1 | 5/2017 | Ghatnekar et al. |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |
| 2017/0145094 A1 | 5/2017 | Galetto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper et al. |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0189450 A1 | 7/2017 | Conway et al. |
| 2017/0190767 A1 | 7/2017 | Schurpf et al. |
| 2017/0191022 A1 | 7/2017 | Lipkens et al. |
| 2017/0232439 A1 | 8/2017 | Suresh et al. |
| 2017/0374730 A1 | 12/2017 | Flores |
| 2018/0000311 A1 | 1/2018 | Lipkens et al. |
| 2018/0000870 A1 | 1/2018 | Britt |
| 2018/0000910 A1 | 1/2018 | Chakraborty et al. |
| 2018/0001011 A1 | 1/2018 | Paschon et al. |
| 2018/0008707 A1 | 1/2018 | Bussmer et al. |
| 2018/0009158 A1 | 1/2018 | Harkness et al. |
| 2018/0009888 A9 | 1/2018 | Baumeister et al. |
| 2018/0009895 A1 | 1/2018 | Smith et al. |
| 2018/0010085 A1 | 1/2018 | Lipkens et al. |
| 2018/0014846 A1 | 1/2018 | Rhee |
| 2018/0015128 A1 | 1/2018 | Britt |
| 2018/0015392 A1 | 1/2018 | Lipkens et al. |
| 2018/0016570 A1 | 1/2018 | Lipkens et al. |
| 2018/0016572 A1 | 1/2018 | Tang |
| 2018/0020295 A1 | 1/2018 | Pander et al. |
| 2018/0021379 A1 | 1/2018 | Galetto et al. |
| 2018/0022798 A1 | 1/2018 | Shurpf et al. |
| 2018/0028683 A1 | 2/2018 | Wong et al. |
| 2018/0043473 A1 | 2/2018 | Helvajian et al. |
| 2018/0049767 A1 | 2/2018 | Gee et al. |
| 2018/0051089 A1 | 2/2018 | Galettto et al. |
| 2018/0051265 A1 | 2/2018 | Cooper |
| 2018/0052095 A1 | 2/2018 | Cumbo et al. |
| 2018/0052147 A1 | 2/2018 | Zeng |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0055997 A1 | 3/2018 | Cabrera et al. |
| 2018/0056095 A1 | 3/2018 | Messerly et al. |
| 2018/0057810 A1 | 3/2018 | Zhang et al. |
| 2018/0058439 A1 | 3/2018 | Locke et al. |
| 2018/0066223 A1 | 3/2018 | Lim |
| 2018/0066224 A1 | 3/2018 | Lipkens et al. |
| 2018/0066242 A1 | 3/2018 | Zhang |
| 2018/0067044 A1 | 3/2018 | Kaduchak et al. |
| 2018/0071363 A1 | 3/2018 | Ghatnekar et al. |
| 2018/0071981 A1 | 3/2018 | Collino et al. |
| 2018/0078268 A1 | 3/2018 | Messerly |
| 2018/0080026 A1 | 3/2018 | Rossi et al. |
| 2018/0085743 A1 | 3/2018 | Yavorsky et al. |
| 2018/0087044 A1 | 3/2018 | Lipkens et al. |
| 2018/0088083 A1 | 3/2018 | Sinha |
| 2018/0092338 A1 | 4/2018 | Hering et al. |
| 2018/0092660 A1 | 4/2018 | Ethicon |
| 2018/0094022 A1 | 4/2018 | Bracewell et al. |
| 2018/0095067 A1 | 4/2018 | Huff et al. |
| 2018/0098785 A1 | 4/2018 | Price et al. |
| 2018/0100134 A1 | 4/2018 | Lim |
| 2018/0100204 A1 | 4/2018 | O'Shea |
| 2018/0130491 A1 | 5/2018 | Mathur |

FOREIGN PATENT DOCUMENTS

| | | | |
|---|---|---|---|
| CN | 104722106 B | 4/2016 | |
| DE | 30 27 433 A1 | 2/1982 | |
| DE | 32 18 488 A1 | 11/1983 | |
| DE | 196 48 519 A1 | 6/1998 | |
| DE | 103 19 467 B3 | 7/2004 | |
| DE | 10 2008 006 501 A1 | 9/2008 | |
| DE | 10 2014 206 823 A1 | 10/2015 | |
| EP | 0 292 470 B1 | 11/1988 | |
| EP | 0 167 406 B1 | 7/1991 | |
| EP | 0 641 606 | 3/1995 | |
| EP | 1 175 931 A1 | 1/2002 | |
| EP | 1 254 669 B1 | 11/2002 | |
| EP | 1 308 724 A2 | 5/2003 | |
| EP | 2 209 545 | 7/2010 | |
| EP | 2150350 B1 * | 4/2012 | ............ B03C 5/028 |
| EP | 270152 A1 | 1/2018 | |

(56) References Cited

FOREIGN PATENT DOCUMENTS

| | | |
|---|---|---|
| EP | 2419511 | 1/2018 |
| EP | 3068888 | 1/2018 |
| EP | 3257600 | 1/2018 |
| EP | 3274453 | 1/2018 |
| EP | 3274454 | 1/2018 |
| EP | 3275894 | 1/2018 |
| EP | 278108 | 2/2018 |
| EP | 3279315 | 2/2018 |
| EP | 3286214 | 2/2018 |
| EP | 2289535 | 3/2018 |
| EP | 2545068 | 3/2018 |
| EP | 2675540 | 3/2018 |
| EP | 2750683 | 3/2018 |
| EP | 2796102 | 3/2018 |
| EP | 3066201 | 3/2018 |
| EP | 3066998 | 3/2018 |
| EP | 3107552 | 3/2018 |
| EP | 3288660 | 3/2018 |
| EP | 3288683 | 3/2018 |
| EP | 3289362 | 3/2018 |
| EP | 3291842 | 3/2018 |
| EP | 3291852 | 3/2018 |
| EP | 3292142 | 3/2018 |
| EP | 3292195 | 3/2018 |
| EP | 3292515 | 3/2018 |
| EP | 3294343 | 3/2018 |
| EP | 3294764 | 3/2018 |
| EP | 3294857 | 3/2018 |
| EP | 3294871 | 3/2018 |
| EP | 3294888 | 3/2018 |
| EP | 3294896 | 3/2018 |
| EP | 3296302 | 3/2018 |
| EP | 3297740 | 3/2018 |
| EP | 3298046 | 3/2018 |
| EP | 3164488 | 4/2018 |
| EP | 3301115 | 4/2018 |
| EP | 3302783 | 4/2018 |
| EP | 3302789 | 4/2018 |
| EP | 3303558 | 4/2018 |
| EP | 3306310 | 4/2018 |
| GB | 2 420 510 A | 5/2006 |
| JP | 9-136090 | 5/1997 |
| KR | 10-2004-0053133 A | 6/2004 |
| KR | 1442486 | 9/2014 |
| RU | 2037327 C1 | 6/1995 |
| RU | 2085933 | 7/1997 |
| SU | 629496 | 10/1978 |
| WO | WO 1987/07178 A1 | 12/1987 |
| WO | WO 89/11899 A1 | 12/1989 |
| WO | WO 90/05008 | 3/1990 |
| WO | WO 95/01214 A1 | 1/1995 |
| WO | WO 97/34643 | 9/1997 |
| WO | WO 1998/017373 | 4/1998 |
| WO | WO 98/50133 A1 | 11/1998 |
| WO | WO 00/41794 | 7/2000 |
| WO | WO 02/072234 A1 | 9/2002 |
| WO | WO 02/072236 A1 | 9/2002 |
| WO | WO-02072236 A1 * | 9/2002 ......... A61M 1/3496 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043044 A1 | 3/2013 |
| WO | WO 2013/043297 A1 | 3/2013 |
| WO | WO 2013/049623 A1 | 4/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | 2013/187382 A1 | 12/2013 |
| WO | WO 2014/014941 A1 | 1/2014 |
| WO | WO 2014/029505 | 2/2014 |
| WO | WO 2014/046605 A1 | 3/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |
| WO | WO 2015/102528 | 7/2015 |
| WO | WO 2016/004398 A2 | 1/2016 |
| WO | WO 2016/124542 | 8/2016 |
| WO | WO 2016/176663 | 11/2016 |
| WO | WO 2016/209082 | 12/2016 |
| WO | WO 2017/041102 | 3/2017 |
| WO | WO 20174201349 | 11/2017 |
| WO | WO 2017218714 | 12/2017 |
| WO | WO 2018/009894 A1 | 1/2018 |
| WO | WO 2018002036 | 1/2018 |
| WO | WO 2018005873 | 1/2018 |
| WO | WO 2018013558 | 1/2018 |
| WO | WO 2018013629 A1 | 1/2018 |
| WO | WO 2018013840 | 1/2018 |
| WO | WO2018014174 | 1/2018 |
| WO | WO2018015561 | 1/2018 |
| WO | WO 20180011600 | 1/2018 |
| WO | WO2018018958 | 2/2018 |
| WO | WO2018021920 | 2/2018 |
| WO | WO2018022158 | 2/2018 |
| WO | WO 2018022513 | 2/2018 |
| WO | WO2018022619 | 2/2018 |
| WO | WO2018022651 | 2/2018 |
| WO | WO2018022930 | 2/2018 |
| WO | WO2018023114 | 2/2018 |
| WO | WO2018024639 | 2/2018 |
| WO | WO2018026644 | 2/2018 |
| WO | WO2018026941 | 2/2018 |
| WO | WO2018028647 | 2/2018 |
| WO | WO 2018034343 | 2/2018 |
| WO | WO2018034885 | 2/2018 |
| WO | WO 2018035141 | 2/2018 |
| WO | WO 2018035423 | 2/2018 |
| WO | WO20180202691 | 2/2018 |
| WO | WO2018034655 | 3/2018 |
| WO | WO 2018038711 | 3/2018 |
| WO | WO 2018039119 | 3/2018 |
| WO | WO 2018039407 | 3/2018 |
| WO | WO 2018039408 | 3/2018 |
| WO | WO 2018039410 | 3/2018 |
| WO | WO 2018039412 | 3/2018 |
| WO | WO 2018039515 | 3/2018 |
| WO | WO 2018045284 | 3/2018 |
| WO | WO 2018049226 | 3/2018 |
| WO | WO 2018050738 | 3/2018 |
| WO | WO 2018057825 | 3/2018 |
| WO | WO 2018063291 | 4/2018 |
| WO | WO 2018081476 | 5/2018 |
| WO | WO 20180814701 | 5/2018 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

Chitale et al.; Understanding the Fluid Dynamics Associated with Macro Scale Ultrasonic Separators; Proceedings of Meetings on Acoustics, May 2015.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

(56) References Cited

OTHER PUBLICATIONS

Grenvall et al.; Concurrent Isolation of Lymphocytes and Granulocytes Using Prefocused Free Flow Acoustophoresis; Analytical Chemistry; vol. 87; pp. 5596-5604; 2015.
Higginson et al.; Tunable optics derived from nonlinear acoustic effects; Journal of Applied Physics; vol. 95; No. 10; pp. 5896-5904; 2004.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Jan. 10, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Li et al.; Electromechanical behavior of PZT-brass unimorphs; J. Am. Ceram. Soc. vol. 82; No. 7; pp. 1733-1740, 1999.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, p. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; Separation of bacterial spores from flowering water in macro-scale cavities by ultrasonic standing waves; submitted/uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et al.; An Industrial-Prototype Acoustic Array for Real-Time Emulsion Layer Detection in Oil Storage Tanks; IEEE Sensors Journal, vol. 9, No. 12, Dec. 2009.
Musiak et al.; Design of a Control System for Acoustophoretic Separation, 2013 IEEE 56$^{th}$ International Midwest Symposium on Circuits and Systems (MWSCAS), Aug. 2013, pp. 1120-1123.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Phys. Org. "Engineers develop revolutionary nanotech water desalination membrane." Nov. 6, 2006. http://phys.org/news82047372.html.
Ponomarenko et al.; Density of states and zero Landau level probed through capacitance of graphene; Nature Nanotechnology Letters, Jul. 5, 2009; DOI: 10.1038/NNANO.2009.177.
"Proceedings of the Acoustics 2012 Nantes Conference," Apr. 23-27, 2012, Nantes, France, pp. 278-282.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al, J. Chem. Edu., 1990, 67(9), p. 763, published Sep. 1990.
Volpin et al.; Mesh simplification with smooth surface reconstruction; Computer-Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-387 (2004).
Wicklund et al.; Ultrasonic Manipulation of Single Cells; Methods in Molecular Biology; vol. 853; pp. 1777-196; 2012.
Annex to Form PCT/ISA/206—Communication Relating to the Results of the Partial International Search Report dated Jul. 18, 2013.
European Search Report of European Application No. 11769474.5 dated Sep. 5, 2013.
European Search Report of European Application No. 11796470.0 dated Jan. 5, 2016.
European Search Report of European Application No. 13760840.2, dated Feb. 4, 2016.
European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.
International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 dated Jun. 21, 2013.
International Search Report and Written Opinion for International Application No. PCT/US2013/032705 dated Jul. 26, 2013.
International Search Report and Written Opinion for International Application No. PCT/US2013/050729 dated Sep. 25, 2013.
International Search Report and Written Opinion for International Application No. PCT/US2013/059640 dated Feb. 18, 2014.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.

(56) References Cited

OTHER PUBLICATIONS

International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
International Search Report and Written Opinion for International Application No. PCT/US2017/030903 dated Jul. 19, 2017.
International Search Report and Written Opinion for International Application No. PCT/US2017/025108 dated Jul. 20, 2017.
International Search Report and Written Opinion for International Application No. PCT/US2017/031425 dated Aug. 30, 2017.
Sony New Release: <http://www.sony.net/SonyInfo/News/Press/201010/10-137E/index.html>.
International Search Report and Written Opinion for International Application No. PCT/US2017/031425 dated Oct. 23, 2017.
Lenshof et al., "Efficient Purification of CD4+ Lymphocytes from Peripheral Blood Progenitor Cell Products Using Affinity Bead Acoustophoresis", Cytometry Part A, 85A, 2014, pp. 933-941.

* cited by examiner

AFFINITY CELL EXTRACTION BY ACOUSTICS

BACKGROUND

Separation of biomaterial has been applied in a variety of contexts. For example, separation techniques for separating proteins from other biomaterials are used in a number of analytical processes.

SUMMARY

Separation of biomaterials can be accomplished by functionalized material distributed in a fluid chamber that bind the specific target materials such as recombinant proteins and monoclonal antibodies or cells. The functionalized material, such as microcarriers that are coated with an affinity protein, is trapped by nodes and anti-nodes of an acoustic standing wave. In this approach, the functionalized material is trapped without contact (for example, using mechanical channels, conduits, tweezers, etc.).

BRIEF DESCRIPTION OF THE DRAWINGS

The drawings are described in more detail below, with reference to the accompanying drawings, in which.

DETAILED DESCRIPTION

The affinity separation of biological materials, such as proteins or cells, is accomplished through the use of a ligand that is covalently bonded to a surface, such as a microbead, interacts with the protein or cell such that the protein or cell is bound to the ligand on the microbead.

A ligand is a substance that forms a complex with the biomolecules. With protein-ligand binding, the ligand is usually a molecule which produces a signal by binding to a site on a target protein the binding typically results in a change of confirmation of target protein. The ligand can be a small molecule, ion, or protein which binds to the protein material. The relationship between ligand and binding partner is a function of charge, hydrophobicity, and molecular structure. Binding occurs by intermolecular forces such as ionic bonds, hydrogen bonds and van der Waals forces. The Association of docking is actually reversible through disassociation. Measurably irreversible covalent bonds between the ligand and target molecule is a typical in biological systems.

A ligand that can bind to a receptor, alter the function of the receptor, and trigger a physiological response is called an agonist for the receptor. Agonist binding to receptor can be characterized both in terms of how much physiological response can be triggered and in terms of the concentration of the agonist that is required to produce the physiological response. High affinity ligand binding implies that the relatively low concentration of the ligand is adequate to maximally occupy a ligand-binding site and trigger a physiological response. The lower the $K_i$ level is, the more likely there will be a chemical reaction between the pending and the receptive antigen. Low-affinity binding (high $K_i$ level) implies that a relatively high concentration of the ligand is required before the binding site is maximally occupy and the maximum physiological response to the ligand is achieved. Bivalent ligands consist of two connected molecules as ligands, and are used in scientific research to detect receptor timers and to investigate the properties.

The T cell receptor, or TCR, is a molecule found on the surface of T cells or T lymphocytes, that is responsible for recognizing fragments of antigen as peptides bound to major histocompatibility complex (MHC) molecules. The binding between TCR and antigen peptides is of relatively low affinity and is degenerative.

Figure 1:
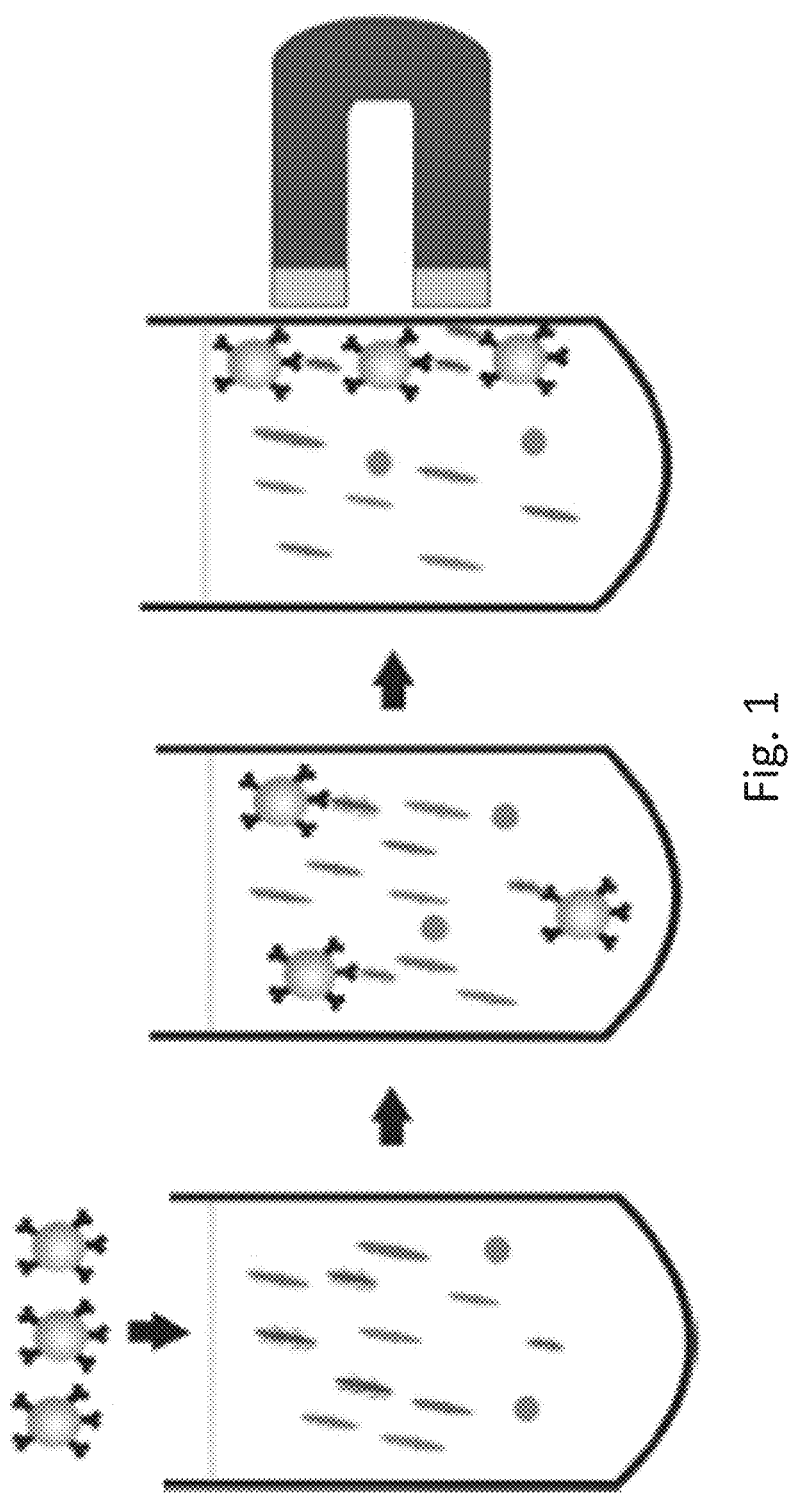
FIG. 1 is a diagram of a separation process using paramagnetic beads in a magnetic field.

Referring to FIG. 1, paramagnetic beads, such as iron or ferro-magnetic beads sold under the name Dynabeads, have been used to achieve affinity extraction. The magnetic beads, coated with a functionalized material, bind to biological targets in complex mixtures to permit the target material to be separated out of the complex mixture using a magnetic field. The beads carry molecules for affine binding various targets with high specificity. The beads are injected into the complex mixture and incubated to bind the targets. The beads are extracted by a magnet together with the targets attached to the beads.

Micro sized beads are available, such as, e.g., Dynabeads, which are on the order of 4.5 μm in size. Nano sized beads may be used, such as, e.g., Myltenyi, which are on the order of 50 nm in size. Some of the affine molecules that may be used include antibodies, aptamers, oligonucleotides and receptors, among others. The targets for the affinity binding may include biomolecules, cells, exosomes, drugs, etc.

Figure 2:
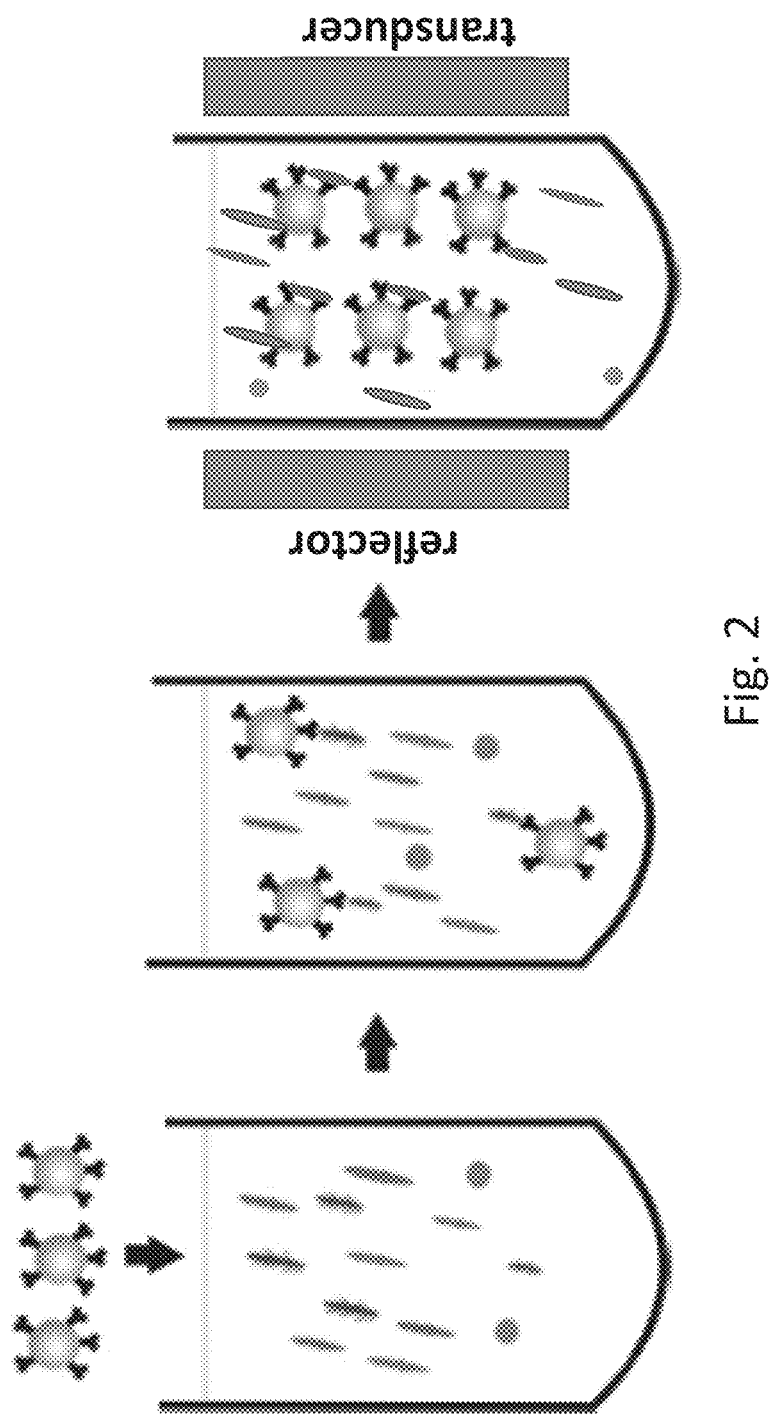
FIG. 2 is a diagram of a separation process using acoustic beads in an acoustic field.

Referring to FIG. 2, beads with high acoustic contrast and affinity chemistry are illustrated. These acoustic beads can be used in exactly the same way as magnetic beads with regard to having functionalized material coatings or composition for affinity binding. The acoustic beads are designed to be extracted from a complex mixture or fluid with an acoustic field. The acoustic beads can be directly used in all the applications developed in cell manufacturing, biochemistry, diagnostics, sensors, etc. that use magnetic beads.

The acoustic beads can use the same surface and affinity chemistry as is used with magnetic beads. This ease of substitution of acoustic beads for magnetic beads has many advantages, including simplifying approval for applications, as well as simplifying the applications.

The acoustic beads can be made biocompatible. Such beads can be produced in different sizes, which permits continuous separation based on size in a size differentiating acoustic field, such as may be provided with an angled-field fractionation technology. The acoustic beads can be combined with an enclosed acoustics-based system, leading to a continuous end-to-end cycle for therapeutic cell manufacturing. This functionality provides an alternative to magnetic bead extraction, while preserving use of currently existing affinity chemistry, which can be directly transferred to the acoustic beads. The acoustic beads may be a consumable product in the separation operation.

In an example, a proof of concept trial was made using the published Memorial Sloan Kettering Cancer Center (MSKCC) protocol for extraction of CD3+ T cells from patient's blood. In the trial, paramagnetic beads were used, and the magnetic field is replaced with an acoustic field. The process of extracting CD3+ T cells from patient's blood is an integral part of manufacturing CAR (chimeric antigen receptor) T cells. Current processes are based on commercially available CD3 Dynabeads. In the trial, efforts were made to minimize the protocol differences, including performing the experiments in culture broth, rather than blood. The difference is considered reduced since several steps in CAR T cell manufacturing work from broth. The solvent density was increased to make T cells "acoustically invisible," or not as susceptible to an acoustic field. The small size of the Dynabeads may provide an acoustic contrast that is similar to the cells, thus making separation tolerances smaller. The trial employed Jurkat CD3+ and CD3– T cell lines as models. The CD3– cells were employed as a control for non-specific trapping.

Figure 4:
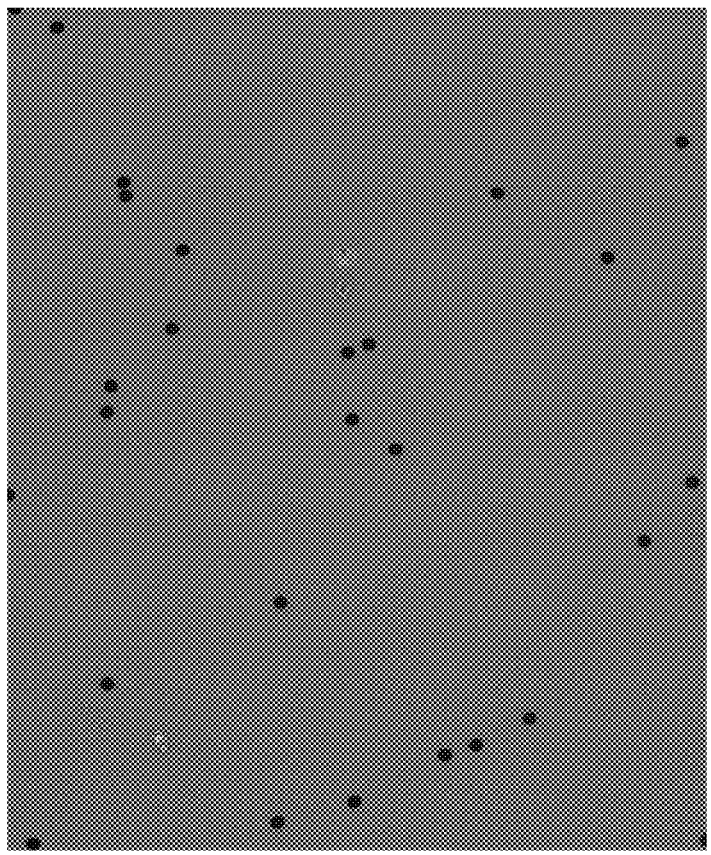
FIG. 4 is an image of beads without CD3− T-cells to demonstrate specificity of selection.
Figure 3:
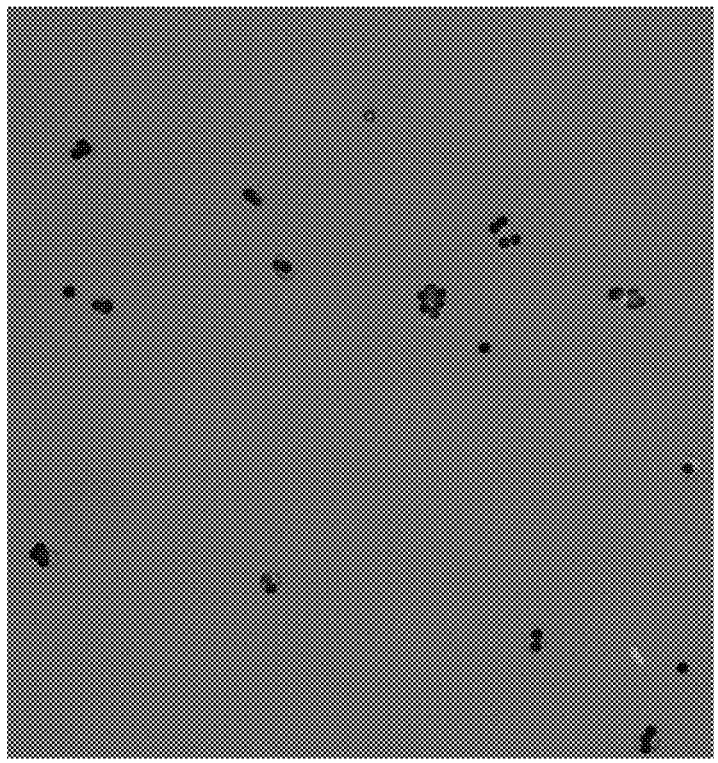
FIG. 3 is an image of CD3+ T-cell complexes with beads.

Referring now to FIGS. 3 and 4, images of results of the trial are shown. The cell suspensions were incubated with CD3 Dynabeads, which bound CD3+ cells. The mixture was passed through the acoustic system, which trapped the magnetic beads (with or without cells). The collected cells were successfully growing in culture. The images in FIGS. 3 and 4 are obtained with overlap of bright field images with fluorescence images. The beads are black with slight reddish autofluorescence. The live cells are fluorescent red. The bead diameter is 4.5 microns. FIG. 3 shows CD3+ T-cell complexes with beads, which demonstrates the efficiency of the technique. FIG. 4 shows that no CD3– T-cells have been extracted, which demonstrates the specificity and selectivity of the technique.

Figure 6:
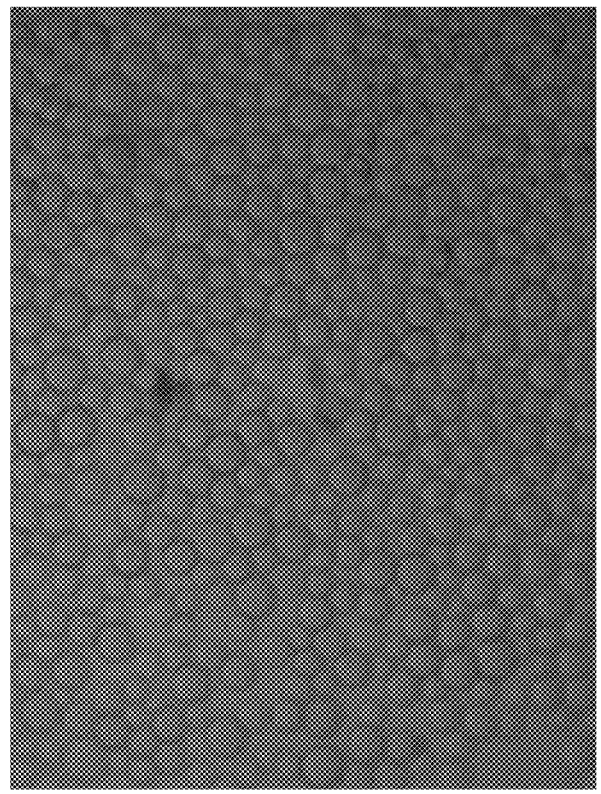
FIG. 6 is an image of homogenous agarose beads.
Figure 5:
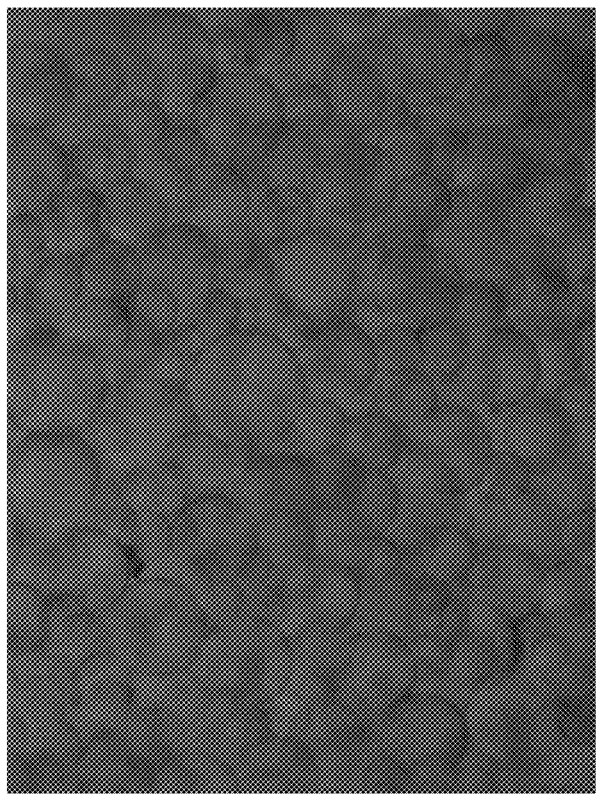
FIG. 5 is an image of heterogenous beads available with streptavidin and biotin conjugates.

Referring now to FIGS. 5 and 6, results of a trial with acoustic beads is shown. In this trial, agarose beads were used as the acoustic beads. These beads are available off-shelf from several manufacturers, and are not paramagnetic or have little to none iron or ferro magnetic content. Some agarose beads have surface modifications that simplify antibody attachment. They are also composed of biocompatible material, which can be important for therapeutic solutions. FIG. 5 shows ABTBeads, which are relatively inexpensive, heterogeneous (20-150 μm), off-shelf beads, which are available with streptavidin and biotin conjugates. FIG. 6 shows CellMosaic agarose beads, which tend to be relatively expensive, homogeneous (20-40 μm), and can be configured with any modification by order.

Figure 7:
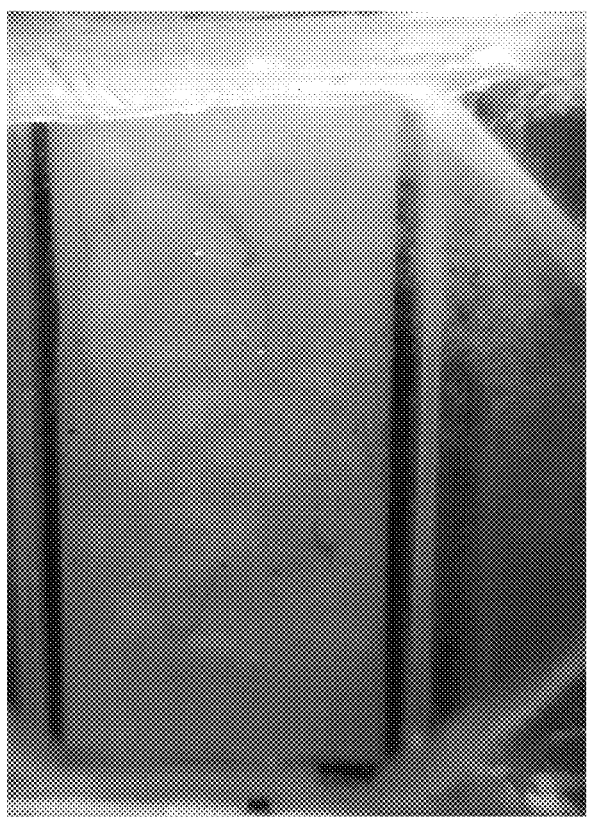
FIG. 7 is a photograph of a miniature acoustic system for processing beads.

The acoustic beads can be trapped in an acoustic field, such as a multi-dimensional acoustic standing wave. Referring to FIG. 7, a miniature acoustic system developed for acoustic applications is shown, which is used for trapping the acoustic beads. The smaller size of the system contributes to reducing the need for larger amounts of expensive reagents and permits processing of small volume samples.

Figure 8:
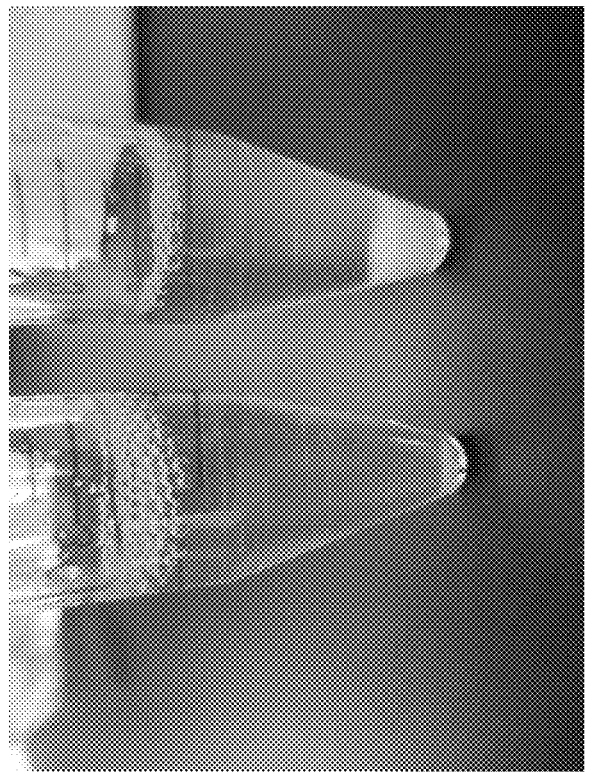
FIG. 8 is a photograph of a separation result.

Referring to FIG. 8, CellMosaic agarose beads escaped (left tube) and trapped (right) in the acoustic system are shown. The acoustic system trapping efficiency can be 90%+.

Figure 9:
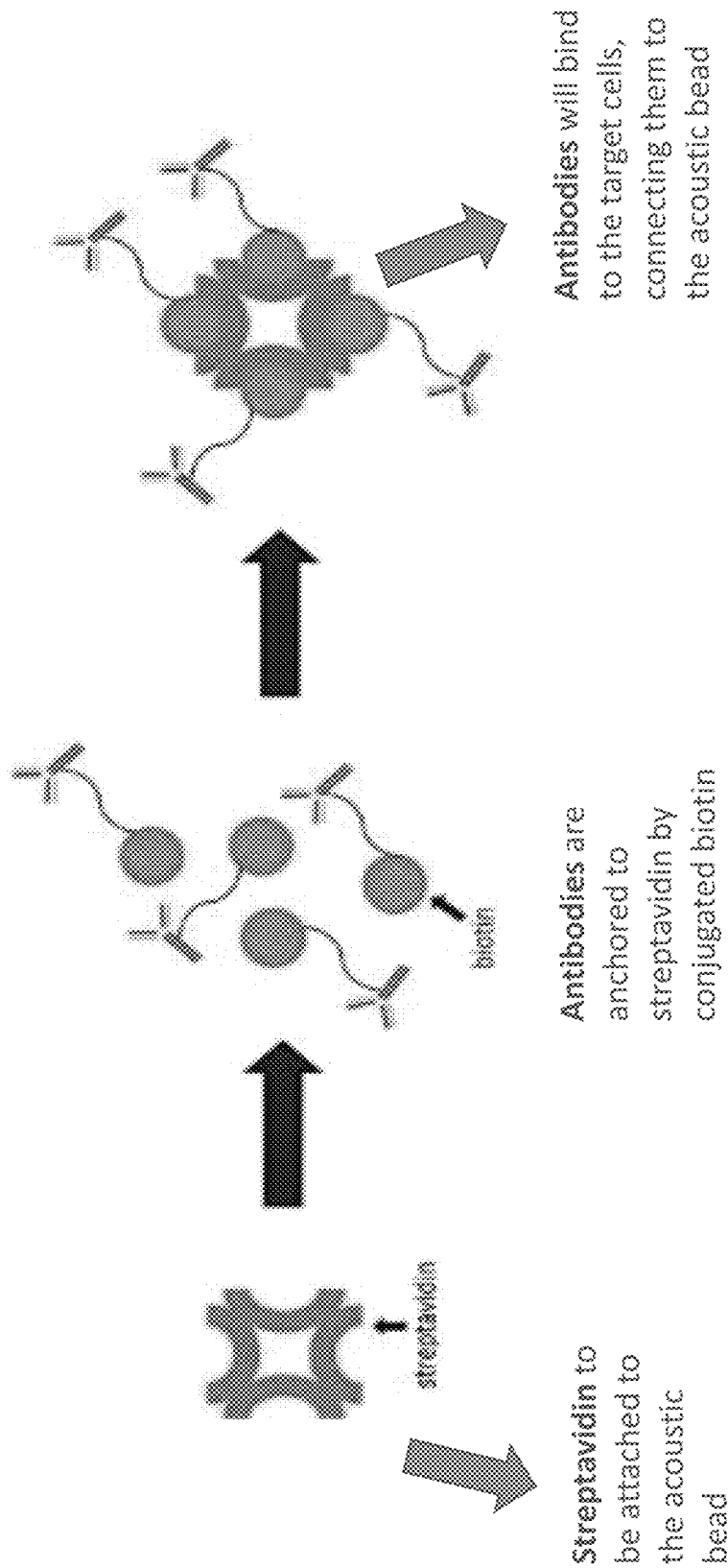
FIG. 9 is a diagram of an affinity technique that may be used with beads.

Referring to FIG. 9, a flexible approach to activating the acoustic beads is illustrated. In this approach, antibodies are attached to agarose beads using a streptavidin-biotin complex. The complex is widely used in biochemistry, and very stable. Agarose beads with conjugated streptavidin are available commercially as are antibody-biotin conjugates.

Figure 10:
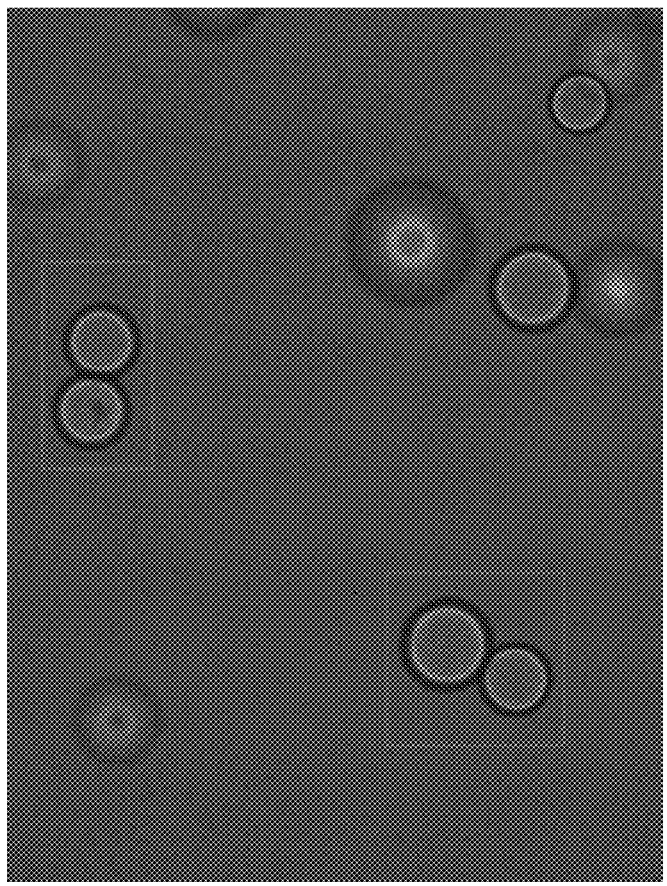
FIGS. 10, 11 and 12 are microphotographs of strepteividin-conjugated and biotin-conjugated beads that form complexes with each other.
Figure 12:
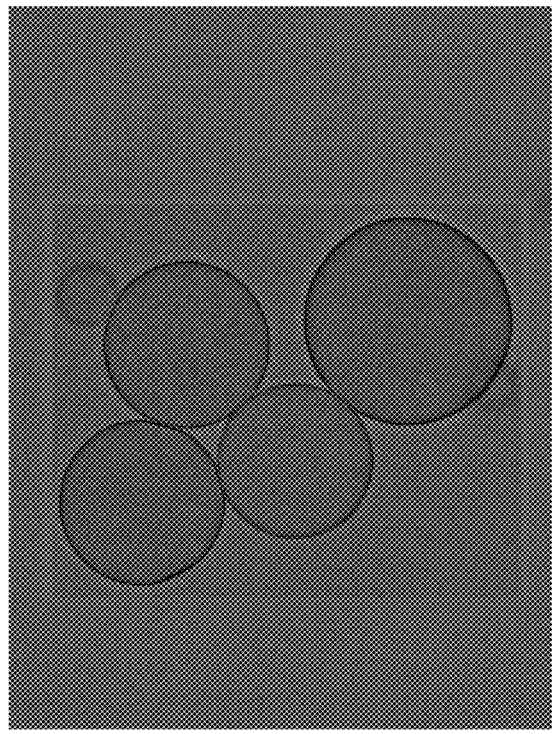
Figure 11:
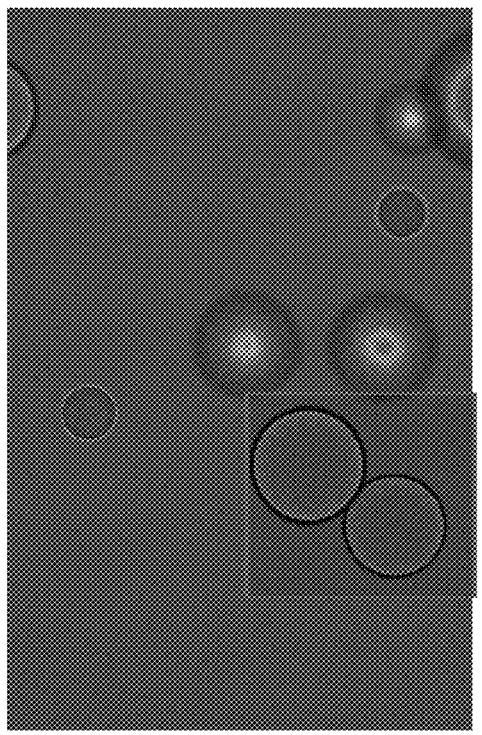
Figure 13:
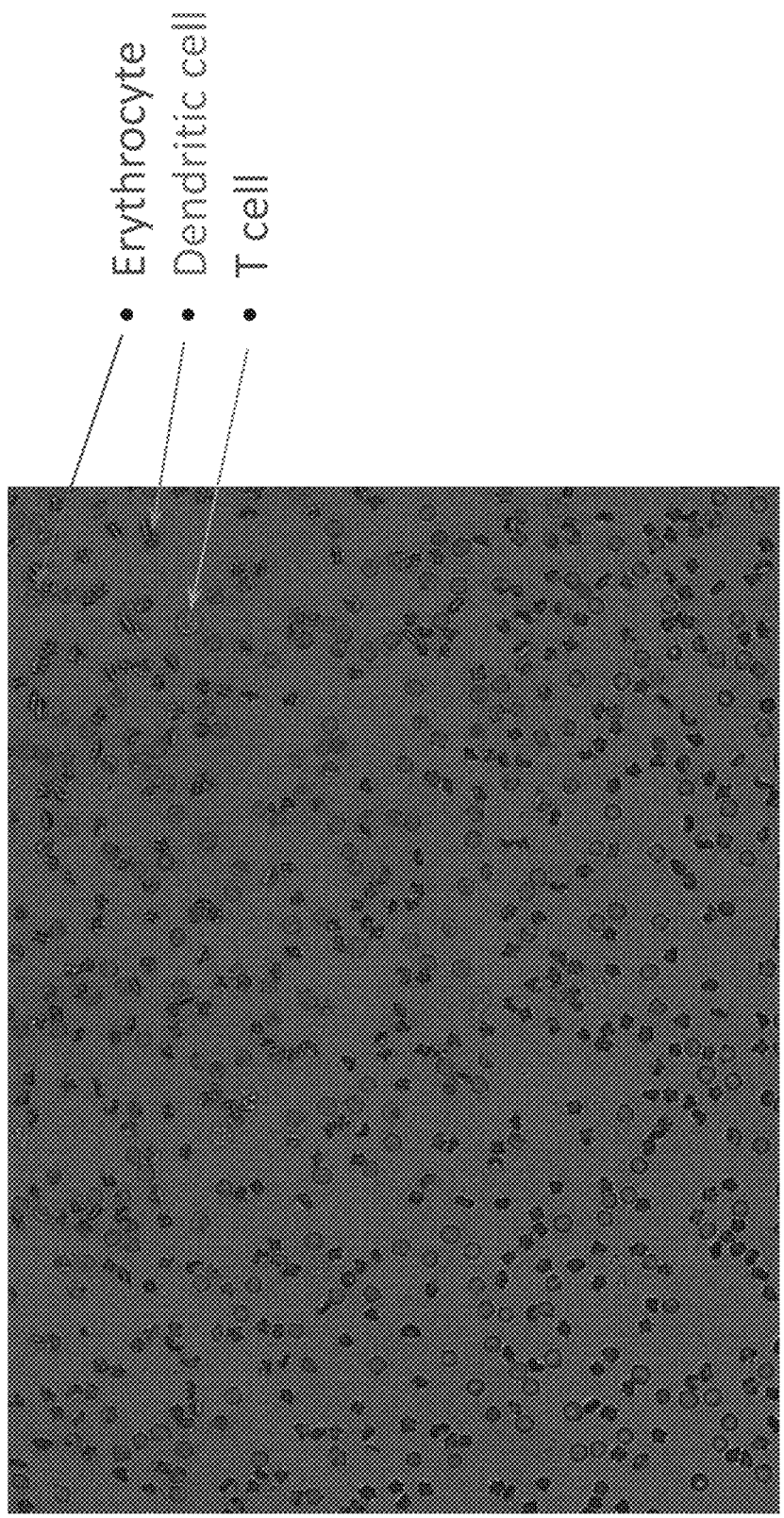
FIG. 13 is a microphotograph of a cell suspension with identification of an Erythrocyte, a Dendritic cell and a T cell.

The functionality of streptavidin-beads & biotin-beads was evaluated. Referring to FIGS. 10-12, streptevidin-conjugated and biotin-conjugated beads are shown to form complexes with each other, as expected, upon mixing, It may be desirable to obtain independent isolation of CD4+ and CD8+ ("helper" and "killer" T cells, respectively) from suspensions and mixing them in desired ratios with a view toward efficient therapy. Toward this end, acoustic beads with affinity for CD4 and CD8 receptors can be provided. A trial to obtain an example was performed with cell suspensions prepared from mice spleens. Referring to FIG. 13, identification of an Erythrocyte, a Dendritic cell and a T cell is provided. About 20 million (M) and 18M CD4+ and CD8+ T-cells, respectively, have been isolated from 4 spleens using Invitrogen depletion kits. Both cell lines can grow, and both CD4 and CD8 T-cells are about 8.2-8.6 μm.

Figure 15:
FIG. 15 is a microphotograph of a bright field image of green fluorescence of anti-CD4 antibodies bound to cells.
Figure 14:
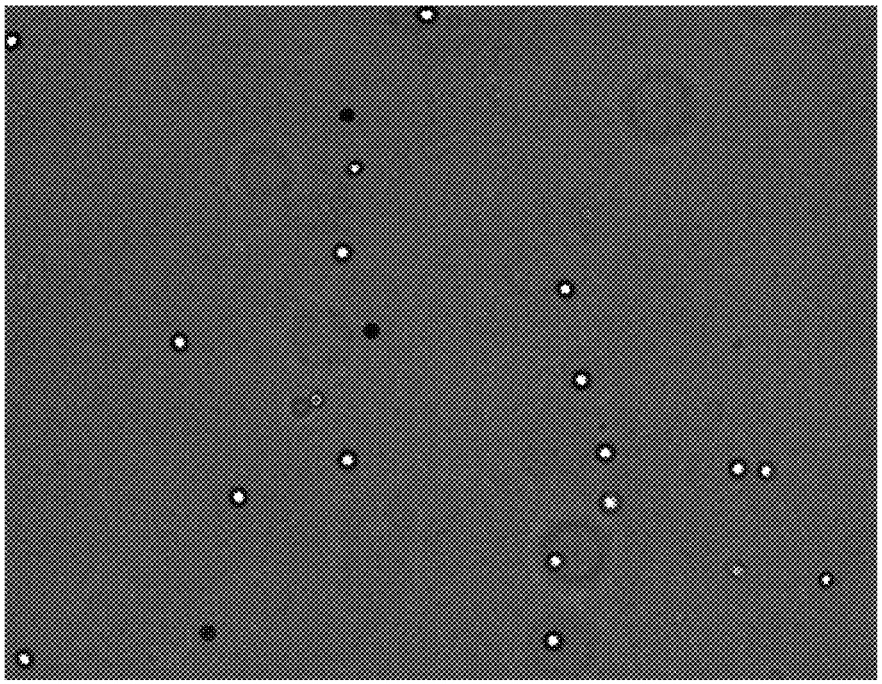
FIG. 14 is a microphotograph of a bright field image of cells.
Figure 16:
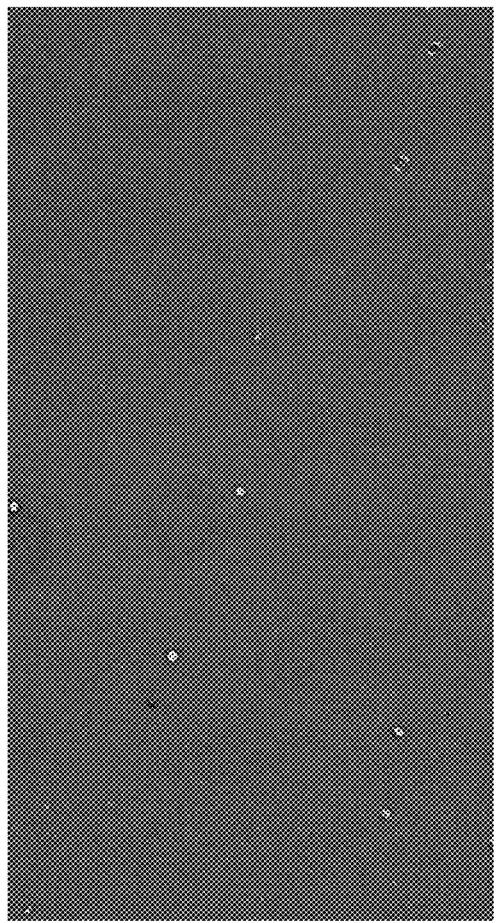
FIG. 16 is a microphotograph of a bright field image of cells.
Figure 17:
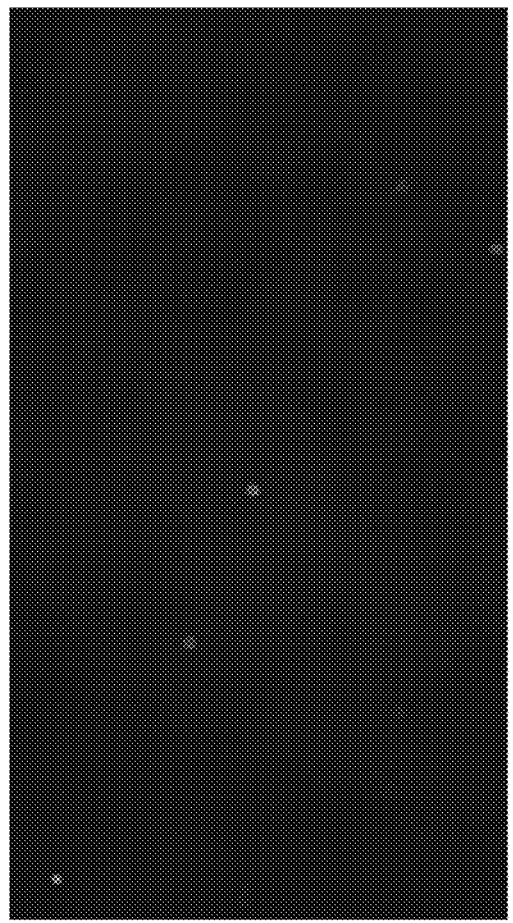
FIG. 17 is a microphotograph of a bright field image of magenta fluorescence of anti-CD4 antibodies bound to cells.

In this trial, CD4+ and CD8+ isolated cells were verified immunologically. Referring to FIGS. 14 and 15, verification of the presence of CD4 receptors is obtained. Alexa488 anti-CD4 antibodies are used to estimate the amount of isolated CD4 T-cells after purification from mouse spleens. FIG. 14 shows a bright field image with small circles being the cells in focal plane. FIG. 15 shows fluorescence of anti-CD4 antibodies bound to the cells. FIG. 16 shows a bright field image with small circles being the cells in focal plane. FIG. 17 shows fluorescence of anti-CD4 antibodies bound to the cells. The different colors of green and magenta in FIGS. 15 and 17, respectively, can allow multiplex analysis of results, e.g., a CD4/CD8 ratio.

Figure 18:
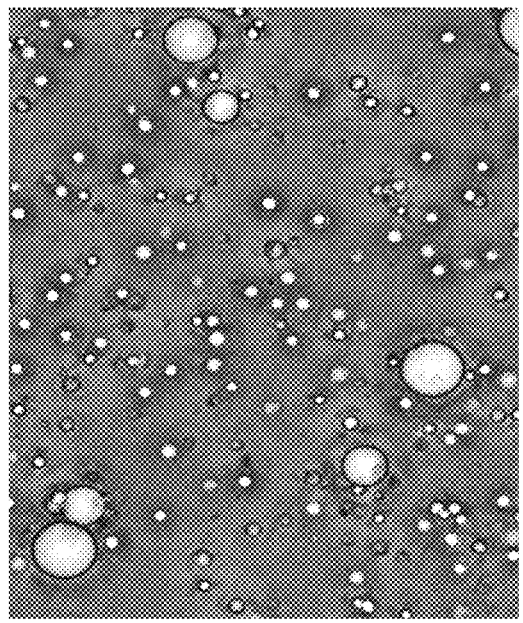
FIG. 18 is a series of microphotographs illustrate examples of bead-cell complexes in environments with an excess of beads and with an excess of cells.
Figure 18:
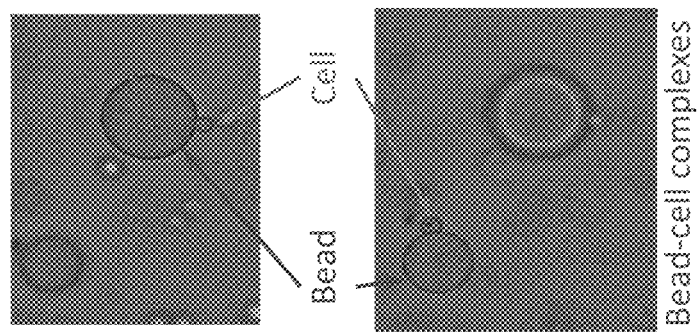
Figure 18:
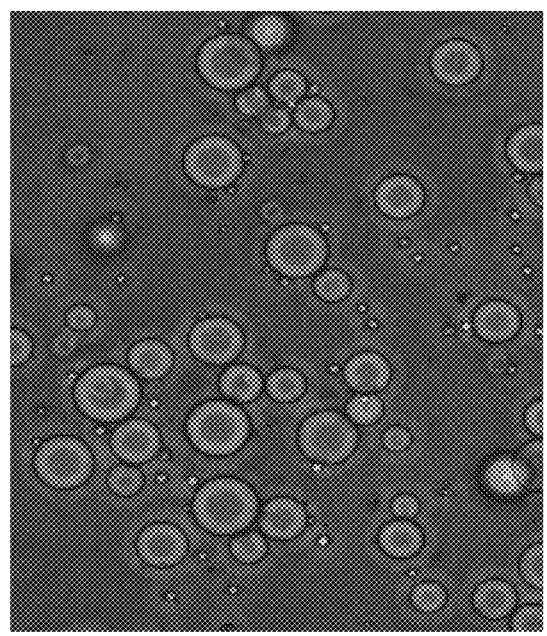

Referring now to FIG. 18, results of the trial are shown where Streptavidin-conjugated agarose beads were employed with biotin-conjugated anti-CD3 antibodies and CD3+ Jurkat T-cells. The affinity combinations of beads and cells is clearly illustrated. The beads can be separated out in an acoustic field to extract the cells from the mixture.

Proof-of-concept and validation of performance has been shown using acoustic affinity beads in an acoustic system. The disclosed methods and systems permit the use of off-shelf reagents, and currently available acoustic systems. The affinities can target any type of desired T cells or markers including CD3+, CD4+, CD8+. The acoustic beads can have a high, neutral or low contrast factor, which can affect how the beads respond to an acoustic field, for example being urged toward an acoustic node or antinode, or passing through the field.

The beads may be composed of various materials and combinations, which permits development of optimal chemistry with acoustic performance and biocompatibility. The beads may be processed for isolation, sorting or any other function useful in a separation process. When used with a tuned acoustic system, the performance of specifically designed acoustic beads can match or exceed that of paramagnetic beads.

Existing chemistries may be used with the acoustic beads, and in conjunction with specifications of size and structure homogeneity to achieve desired results for acoustic and for isolation performance. The beads may be composed of composite constructs to advance acoustic efficiency. The acoustic system provides flexibility to manage small sizes, with heat management, and the use of fluidics to obtain results that are not possible with paramagnetic beads alone. The biocompatibility and/or biodegradability of the acoustic beads and simplified processing permits integration with existing hardware for CAR T cell manufacturing. The affinity acoustic beads can be used in a number of environments, including model environments such as, e.g., animal blood spiked with target cells and murine spleen extracts. The acoustic beads may thus be used in collaboration with existing systems, and may be designed and manufactured for target applications. The beads may be provided with a core that is acoustically active or neutral, and the bead themselves may be configured for high, neutral or low acoustic contrast. The size of the beads may be configured for separation and affinity in combination, for example a certain sized bead may include functionalized material to target a certain biomaterial, while another sized bead, may be functionalized to target another biomaterial, each of which can be separated simultaneously and continuously in a closed or flowing system. The beads can be designed to be of a homogeneous size distribution within a narrow or relatively broad range. Various affinity chemistries may be used, including streptavidin-biotin complex and immunoglobulin or aptamer. The beads may be designed for ease of manufacturability and/or for shelf-life. The beads may be used with approved chemistries, so that they may readily be integrated into known systems that use approved chemistries.

Figure 19:
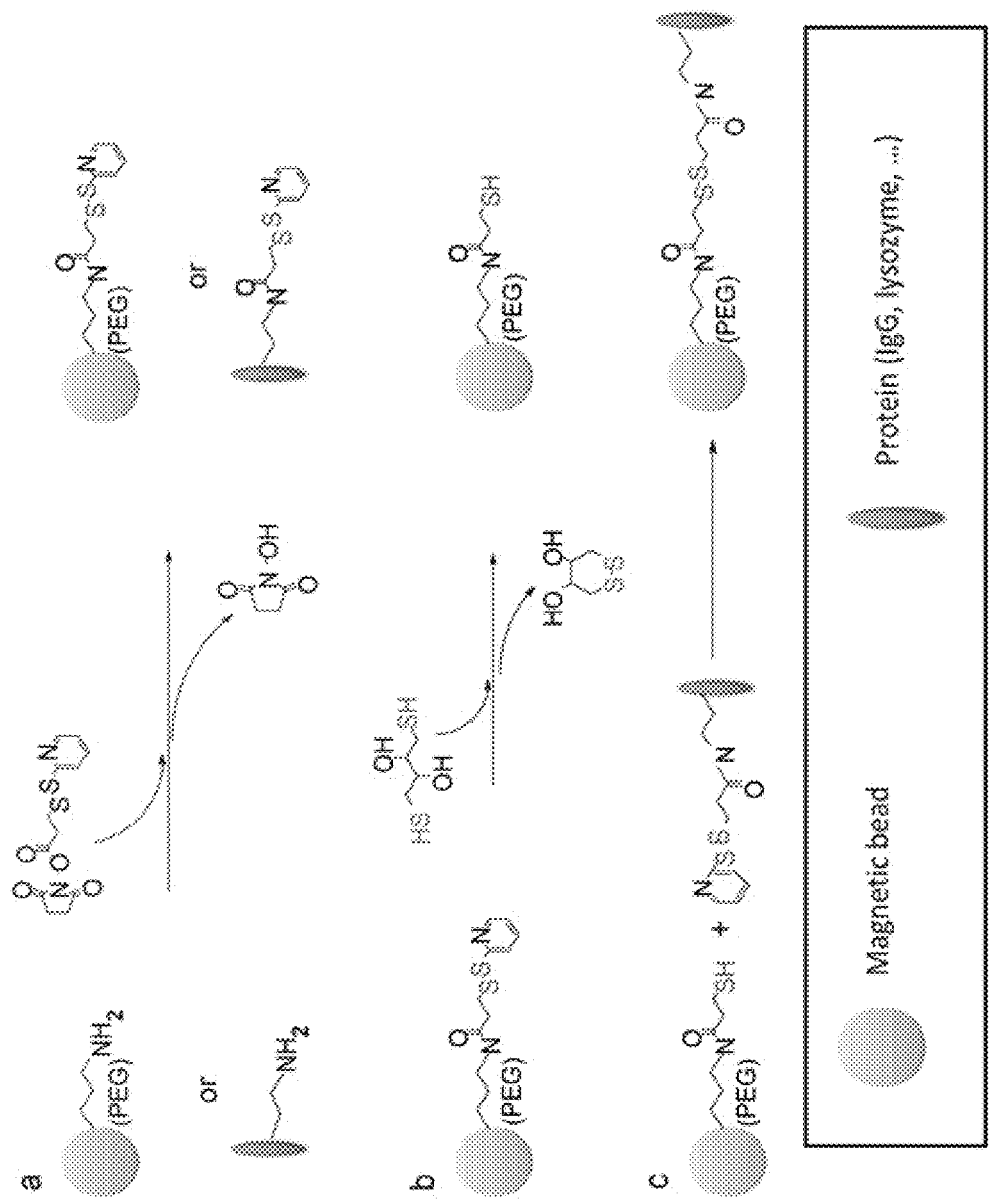
FIG. 19 is a diagram of example activation chemistries for affinity binding.

Referring to FIG. 19, an illustration of example activation chemistries is shown. The activation chemistries illustrated are applicable to the acoustic affinity beads described herein.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known processes, structures, and techniques have been shown without unnecessary detail to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional stages or functions not included in the figure.

Having described several example configurations, various modifications, alternative constructions, and equivalents may be used without departing from the spirit of the disclosure. For example, the above elements may be components of a larger system, wherein other structures or processes may take precedence over or otherwise modify the application of the invention. Also, a number of operations may be undertaken before, during, or after the above elements are considered. Accordingly, the above description does not bound the scope of the claims.

What is claimed is:

1. A method for separating material in a fluid, comprising:
    applying a functionalized material to a plurality of non-magnetic biodegradable agarose beads that are acoustically responsive;
    in the fluid, exposing the beads to biomaterial with an affinity for the functionalized material to permit the biomaterial to bind to the beads, wherein the biomaterial is T cells; and
    exposing the beads in the fluid to an acoustic field and trapping the beads in the acoustic field.

2. The method of claim 1, wherein the functionalized material is a streptavidin conjugate or a biotin conjugate.

3. The method of claim 1, wherein the functionalized material is composed with an affinity for one or more of CD3, CD4 or CD8 receptors.

4. The method of claim 1, wherein the functionalized material includes affine molecules that are one or more of antibodies, aptamers or oligonucleotides.

5. The method of claim 1, wherein the functionalized material comprises a ligand.

6. The method of claim 1, further comprising reversing a binding between the biomaterial and the beads.

7. The method of claim 1, further comprising:
    a first biomaterial and a distinct second biomaterial included in the biomaterial;
    isolating the first biomaterial and isolating the second biomaterial; and
    combining the first biomaterial and the second biomaterial in a predetermined ratio.

8. The method of claim 1, further comprising:
    targeted material and other material included in the biomaterial; and
    providing beads with an affinity for the targeted material to the fluid.

9. The method of claim 8, further comprising increasing a density of the fluid to modify an acoustic contrast between the T cells and the fluid.

10. The method of claim 1, wherein the plurality of beads include at least two different sizes of beads, each size being configured with an affinity for a different type of biomaterial.

11. A method for separating material in a fluid, comprising:
    generating an acoustic standing wave in a chamber suitable for housing a fluid;
    providing non-magnetic bead-biomaterial complexes to the chamber, wherein the beads are acoustically responsive non-magnetic biodegradable agarose beads, the biomaterial is T cells and the T cells are bound to the beads via a functionalized material with an affinity for the T cells; and
    in the fluid, trapping the non-magnetic bead-biomaterial complexes in the acoustic standing wave.

12. The method of claim 11, wherein the acoustic standing wave is a multidimensional acoustic standing wave.

13. The method of claim 11, further comprising binding the biomaterial to the non-magnetic beads to form the bead-biomaterial complexes prior to being provided to the chamber.

14. The method of claim 11, further comprising trapping greater than 90% of the non-magnetic bead-biomaterial complexes in the acoustic standing wave.

* * * * *